US012268435B2

(12) United States Patent
Sliwa et al.

(10) Patent No.: US 12,268,435 B2
(45) Date of Patent: *Apr. 8, 2025

(54) ULTRASONIC LESION FEEDBACK, ANTIPOP MONITORING, AND FORCE DETECTION

(71) Applicant: St. Jude Medical, LLC, Abbott Park, IL (US)

(72) Inventors: John W. Sliwa, Los Altos Hills, CA (US); Zhenyi Ma, Santa Clara, CA (US); Stephen A. Morse, Menlo Park, CA (US)

(73) Assignee: ST. JUDE MEDICAL, LLC, Abbott Park, IL (US)

( * ) Notice: Subject to any disclaimer, the term of this patent is extended or adjusted under 35 U.S.C. 154(b) by 1182 days.

This patent is subject to a terminal disclaimer.

(21) Appl. No.: 17/097,996

(22) Filed: Nov. 13, 2020

(65) Prior Publication Data

US 2021/0137577 A1    May 13, 2021

Related U.S. Application Data

(60) Continuation of application No. 15/637,896, filed on Jun. 29, 2017, now Pat. No. 10,864,034, which is a
(Continued)

(51) Int. Cl.
*A61B 8/12* (2006.01)
*A61B 8/00* (2006.01)
(Continued)

(52) U.S. Cl.
CPC ........... *A61B 18/1492* (2013.01); *A61B 8/12* (2013.01); *A61B 8/429* (2013.01); *A61B 8/445* (2013.01);
(Continued)

(58) Field of Classification Search
CPC ........... A61B 8/12; A61B 8/429; A61B 8/445; A61B 8/4466; A61B 18/1492; A61B 2090/065
See application file for complete search history.

(56) References Cited

U.S. PATENT DOCUMENTS 5,271,402 A    12/1993   Yeung et al.
5,284,148 A    2/1994    Dias et al.
(Continued)

FOREIGN PATENT DOCUMENTS

CN    102348424    2/2012
EP    2477572      1/2013
(Continued)

OTHER PUBLICATIONS

International Search Report and Written Opinion for PCT/US2013/032168, dated May 31, 2013.

*Primary Examiner* — Colin T. Sakamoto
(74) *Attorney, Agent, or Firm* — Wiley Rein LLP (57) ABSTRACT

An ablation catheter comprises: an elongated catheter body extending longitudinally between a proximal end and a distal end along a longitudinal axis; a distal member disposed adjacent the distal end, the distal member including an ablation element to ablate a biological member; one or more acoustic transducers disposed in the distal member and each configured to direct an acoustic signal toward a respective target ablation region and receive reflection echoes therefrom; and an acoustic redirection member disposed in the distal member to at least partially redirect the acoustic signal from at least one of the acoustic transducers toward a tissue target. The distal member includes a most-distal portion, a proximal portion, and a deflectable portion between the most-distal portion and proximal portion to permit deflection between the most-distal portion and proximal portion of
(Continued)

the distal member. The transducers and redirection member are mounted on opposite sides of the deflectable portion.

20 Claims, 4 Drawing Sheets

Related U.S. Application Data (60) division of application No. 14/394,164, filed as application No. PCT/US2013/032168 on Mar. 15, 2013, now Pat. No. 9,717,547.

(60) Provisional application No. 61/636,767, filed on Apr. 23, 2012.

(51) Int. Cl.
*A61B 18/12* (2006.01)
*A61B 18/14* (2006.01)
*A61B 90/00* (2016.01)
*A61B 17/00* (2006.01)
*A61B 18/00* (2006.01)

(52) U.S. Cl.
CPC .............. *A61B 18/12* (2013.01); *A61B 90/06* (2016.02); *A61B 2017/00106* (2013.01); *A61B 2018/00577* (2013.01); *A61B 2090/061* (2016.02); *A61B 2090/065* (2016.02); *A61B 2090/3784* (2016.02); *A61B 2218/002* (2013.01)

(56) References Cited

U.S. PATENT DOCUMENTS

| | | |
|---|---|---|
| 5,313,950 A | 5/1994 | Ishikawa et al. |
| 5,588,432 A | 12/1996 | Crowley |
| 5,651,366 A | 7/1997 | Liang |
| 2003/0125730 A1 | 7/2003 | Berube et al. |
| 2004/0147920 A1 | 7/2004 | Keidar |
| 2009/0099551 A1 | 4/2009 | Tung et al. |
| 2011/0144491 A1 | 6/2011 | Sliwa |
| 2011/0313290 A1 | 12/2011 | Weekamp et al. |
| 2012/0095371 A1 | 4/2012 | Sverdlik et al. |
| 2012/0165669 A1 | 6/2012 | Barley et al. |
| 2012/0265069 A1 | 10/2012 | Sliwa et al. |
| 2012/0265192 A1 | 10/2012 | Sliwa et al. |

FOREIGN PATENT DOCUMENTS

| | | |
|---|---|---|
| JP | H07-037110 | 7/1995 |
| WO | 2011/033421 | 3/2011 |

ULTRASONIC LESION FEEDBACK, ANTIPOP MONITORING, AND FORCE DETECTION

This application is a continuation of U.S. application Ser. No. 15/637,896, filed 29 Jun. 2017 (the '896 application), now pending, which is a divisional of U.S. application Ser. No. 14/394,164, filed 13 Oct. 2014 (the '164 application), now U.S. Pat. No. 9,717,547, which is a national stage entry of PCT/US13/32168, filed 15 Mar. 2013 (the '168 PCT), now expired, which in turn claims the benefit of U.S. provisional application No. 61/636,767, filed 23 Apr. 2012 (the '767 application). The '896 application, '164 application, the '168 PCT, and the '767 application are each hereby incorporated by reference as though fully set forth herein.

BACKGROUND OF THE INVENTION

The present invention relates generally to catheters for ablation or the like and, more particularly, to a disposable catheter with low COGS, ultrasonic lesion feedback, antipop monitoring, and force detection, and to a dual transducer with forward and side looking ultrasonic lesion feedback and optional force detection.

BRIEF SUMMARY OF THE INVENTION

Embodiments of the invention provide a force sensing catheter and supporting system for therapeutic or diagnostic applications. A catheter includes an elongated flexible catheter body having a distal end and a proximal end, a therapeutic or diagnostic tip on the distal end of the catheter body, and a catheter control handle or manipulation mechanism coupled to the proximal end of the catheter body. The tip region includes a most distal rigid tip portion mounted upon a more proximal abutting semi-rigid tip portion, the semi-rigid portion having known stiffness versus deflection (providing some useful tissue conforming behavior of the semi-rigid tip portion); and (i) an acoustic mirror, window, or membrane, and (ii) an acoustic transducer. The transducer is arranged to emit and receive an acoustic beam or ping which has been at least partially reflected from the mirror, window or membrane. Forces applied to the tip by contacting tissue cause the most distal rigid tip portion to deflect as a rigid whole because it is mounted upon the more proximal semi-rigid deflectable tip portion which angularly and axially deflects slightly but detectably. One of the (i) mirror/window/membrane or (ii) transducer is mounted in the most distal rigid portion and the other is mounted proximally to some or all of the semi-rigid portion (such as, for instance, a rigid proximal portion of the tip region). The transducer is thereby capable of detecting axial and/or angular bending deflections via the changing amplitude and/or time delay of reflections of the acoustic beam or ping reflected from the most distal rigid tip portion mounted upon and bodily movable upon said semi-rigid but deflectable intervening more-proximal tip portion. The catheter system computes from models or retrieves from lookup tables the force(s) which correlate with the system-observed tip deflections via the known angular stiffness and axial stiffness of the semi-rigid portion. The system reports or otherwise utilizes the force for a procedural control, recording, or safety reason.

The inventive catheter will provide all of antipop monitoring, lesion feedback, and preferably both bending and axial force component magnitudes and their net vector sum. In principle, any so-equipped catheter may provide any one or more of lesion progress feedback, antipop monitoring, and force detection. In addition, the catheter may include dual opposed transducers, one forward looking and one backward/side looking via reflective redirection of its beam, which share a common attenuative backer block between them. By placing these opposed-facing transducers on a flexible tip one may also optionally utilize the ultrasound/mirror arrangement to measure force upon tissue. Such a device gives two excellent views of possible tissue targets rather than a single compromise view such as that given by 45 degree devices.

In accordance with an aspect of the present invention, an ablation catheter with acoustic monitoring comprises: an elongated catheter body extending longitudinally between a proximal end and a distal end along a longitudinal axis; a distal member disposed adjacent the distal end, the distal member including an ablation element to ablate a biological member at a target region outside the catheter body; one or more acoustic transducers disposed in the distal member and each configured to direct an acoustic signal toward a respective target ablation region and receive reflection echoes therefrom; and an acoustic redirection member disposed in the distal member to at least partially redirect the acoustic signal from at least one of the acoustic transducers toward a tissue target. The distal member includes a most-distal portion, a proximal portion, and a deflectable portion between the most-distal portion and the proximal portion to permit deflection between the most-distal portion and the proximal portion of the distal member, the deflectable portion being more deflectable than at least one of the most-distal portion or the proximal portion. For the distal member, (i) the one or more acoustic transducers are mounted to the most-distal portion and the acoustic redirection member is mounted to the proximal portion, or (ii) the one or more acoustic transducers are mounted to the proximal portion and the acoustic redirection member is mounted to the most-distal portion of the distal member.

In some embodiments, the most-distal portion of the distal member has no axial deflection and no bending deflection occurring within its own confines. The proximal portion of the distal member has no axial deflection and no bending deflection occurring within its own confines. The deflectable portion of the distal member, within its own confines, permits at least one of axial deflection along the longitudinal axis or bending deflection between the most-distal portion and the proximal portion of the distal member. The axial deflection is less than about 1 mm under an axial force of less than about 100 grams. The bending deflection is less than about 10 degrees under a bending moment of about 200 gram-millimeters. The deflectable portion of the distal member includes one of a laser machined metallic tube with cuts, a metallic tube with cuts machined by wet etching, a metallic tube with cuts machined by EDM (electric discharge machining), a polymeric tube, a braided tube, a woven tube, a convoluted tubular member, a mesh tube, a honeycombed tube, a wave washer, or a tubular member having bellows. At least one of the acoustic transducers is configured to detect a deflection via at least one of an amplitude change or a phase or time-delay change of a reflection of an acoustic signal reflected back from the acoustic redirection member.

In specific embodiments, an acoustic reflection member is mounted to the same portion of the distal member as the acoustic redirection member and being configured to partially reflect an acoustic signal from at least one acoustic transducer of the acoustic transducers back to the at least one acoustic transducer. The at least one acoustic transducer is configured to detect a deflection via at least one of an amplitude change or a phase or time-delay change of a reflection of the acoustic signal reflected back from the acoustic reflection member. The acoustic reflection member comprises one of a partially reflective membrane or a partially reflective prism.

In some embodiments, a controller is operable to determine, based on the detected deflection and a related force-deflection relationship of the deflectable portion of the distal member, a force between the distal member and the biological member. The acoustic signal comprises an acoustic beam or an acoustic ping. The one or more transducers comprise a sideways-redirected acoustic transducer to produce an acoustic signal that is redirected in a beam emanation direction nonparallel to the longitudinal axis to monitor a sideways-formed lesion, and a forward-directed acoustic transducer to produce another acoustic signal that is directed in another direction generally parallel to the longitudinal axis to monitor a forward-facing lesion, respectively.

Another aspect of the invention is directed to an acoustic monitoring method for an ablation procedure using an ablation catheter which includes an elongated catheter body extending longitudinally between a proximal end and a distal end along a longitudinal axis; a distal member disposed adjacent the distal end, the distal member including an ablation element to ablate a biological member at a target region outside the catheter body; one or more acoustic transducers disposed in the distal member and each configured to direct an acoustic signal toward a respective target ablation region and receive reflection echoes therefrom; and an acoustic redirection member disposed in the distal member to at least partially redirect the acoustic signal from at least one of the acoustic transducers toward a tissue target. The distal member includes a most-distal portion, a proximal portion, and a deflectable portion between the most-distal portion and the proximal portion to permit deflection between the most-distal portion and the proximal portion of the distal member, the deflectable portion being more deflectable than at least one of the most-distal portion or the proximal portion. For the distal member, (i) the one or more acoustic transducers are mounted to the most-distal portion and the acoustic redirection member is mounted to the proximal portion, or (ii) the one or more acoustic transducers are mounted to the proximal portion and the acoustic redirection member is mounted to the most-distal portion of the distal member. The method comprises: ablating the biological member at the target region with the ablation element; directing one or more acoustic signals to the biological member and receiving reflection echoes from the biological member by the one or more acoustic transducers, the one or more acoustic signals including an acoustic signal directed toward the tissue target by the acoustic redirection member; and detecting a deflection between the most-distal portion and the proximal portion of the distal member based on reflection of an acoustic signal reflected back to at least one of the acoustic transducers.

In some embodiments, the detecting comprises detecting a deflection via at least one of an amplitude change or a phase or time-delay change of a reflection of an acoustic signal reflected back from the acoustic redirection member to at least one of the acoustic transducers. In some other embodiments, the detecting comprises detecting a deflection via at least one of an amplitude change or a phase or time-delay change of a reflection of an acoustic signal reflected back from an acoustic reflection member to at least one of the acoustic transducers, the acoustic reflection member being mounted to the same portion of the distal member as the acoustic redirection member and partially reflecting the acoustic signal back to the at least one acoustic transducer.

In specific embodiments, the acoustic monitoring method further comprises determining, based on a detected deflection and a related force-deflection relationship of the deflectable portion of the distal member, a force between the distal member and the biological member. The directing comprises at least one of: directing a first acoustic signal from a first acoustic transducer in a direction generally parallel to the longitudinal axis to the acoustic redirection member which redirects the first acoustic signal in a transverse direction nonparallel to the longitudinal axis to monitor a sideways-formed lesion; or directing a second acoustic signal from a second acoustic transducer in a forward direction generally parallel to the longitudinal axis to monitor a forward-facing lesion. Directing one or more acoustic signals to the biological member and receiving reflection echoes from the biological member by the one or more acoustic transducers comprises at least one of acoustic lesion feedback of the biological member being ablated, a tissue thickness measurement in a region of the biological member being ablated, a tissue proximity measurement in a region of the biological member being ablated, a pre-pop warning of the biological member being ablated, or a pre-pop detection of the biological member being ablated.

These and other features and advantages of the present invention will become apparent to those of ordinary skill in the art in view of the following detailed description of the specific embodiments.

DETAILED DESCRIPTION OF THE INVENTION

In the following detailed description of the invention, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment," "this embodiment," or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Exemplary embodiments of the invention, as will be described in greater detail below, provide apparatuses, methods and computer programs for ultrasonic lesion feedback, antipop monitoring, and net force magnitude and direction detection.

Ultrasonic Feedback with Single Acoustic Transducer in Semi-Rigid Catheter Tip

One aspect of this invention is to utilize an acoustic lesion feedback transducer to also measure distortions of a distortable tip having known (but very slight) spring behavior. How to do that for both axial and bending forces using a single spring is not obvious if one has in mind a very flexible tip made flexible to conform to tissue such as a Coolflex™ tip. Thus, tissue conforming tips teach away from the invention.

Embodiments of the invention utilize a minimally flexible or semi-rigid tip (defined below) which is just flexible enough that its slight bending/compression with loading can be detected using a transducer/mirror arrangement; however, it is not so flexible that the ultrasonic beam angles between transducer and mirror change significantly (to a gross tissue conforming extent). In this way, one can track the force-induced slight axial compression and radial bending deflections as small time-delay changes (for axial deflections) and small reflection magnitude changes (for radial deflections). Further, one can retain in view, despite the deflections, the bulk of the tissue echogram coming from within the tissue which varies only with tissue necrosis or microbubbling. Note specifically that the semi-rigid tip is not useable to achieve gross tissue conformance. It will be apparent to one skilled in the art that angulating reflecting or redirecting mirrors will result in both time-delay changes and amplitude changes and these effects can combine to cause reflective peaks to both predictably broaden/narrow and/or to change amplitude depending on the geometries involved.

It is critical that this catheter tip, to the human eye, is essentially rigid even though it will have laser cuts (or some other features of flexibility) which allow very slight distortions just large enough that they can be acoustically detected and correlated to a tiny deflection of a "stiff spring" section. We anticipate an angular distortion on the order of a degree or a few degrees (e.g., ±about 5 degrees) maximum and an axial distortion on the order of a fraction of a millimeter (e.g., a few hundred microns).

In technical terms, the term "semi-rigid" means that one needs to use a deflection-detecting transducer which has a high enough frequency such that the maximum axial distortion is on the order of at least about a half wavelength. For example, one may use a transducer which is centered at about 10 MHz to about 16 MHz. For typical axial load ranges of about 5-50 grams, it may be desirable to have about a half wavelength of axial deflection, and for sideways radial loads of the same magnitude, it may be desirable to have angular distortions of about one degree or a few degrees. In a preferred embodiment, an A/D (analog-digital) digitizer has a minimum digitization rate of 100 MHz and a rate of about 200-500 MHz with at least effective 8-bits of amplitude resolution is preferred. The higher sampling frequency gives better time (versus sample amplitude) resolution so that one can detect small axial distortions causing time delay changes as well as small angular distortions causing mostly amplitude changes.

Figure 1A:
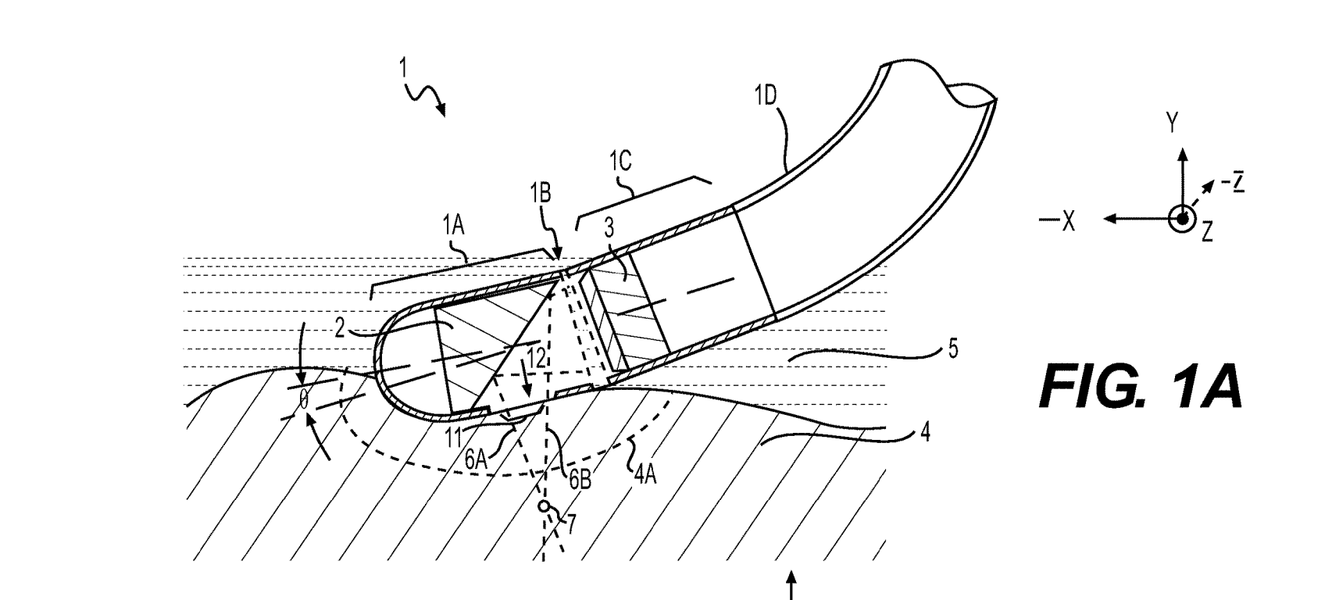
FIG. 1A shows an inventive catheter tip region depicting ultrasonic lesion feedback plus simultaneous force measurement using the same transducer and acoustic mirror tip deflected upon endocardial tissue.

FIG. 1A shows a sectional view of an ablation catheter according to an embodiment of the invention. The catheter includes a flexible body 1$d$ connected to an ablator tip 1 which has a rigid most-distal tip portion (acoustic mirror portion) 1$a$ including an acoustic reflection/redirection member (mirror, window, membrane) 2, an intermediate more-proximal semi-rigid portion 1$b$ acting as a stiff spring, and a rigid most proximal tip portion 1$c$. Ideally, the rigid most-distal portion 1$a$ has no internal axial deflection and no internal bending deflection (occurring within its own confines) and the rigid proximal tip portion 1$c$ has no internal axial deflection and no internal bending deflection (occurring within its own confines). All such bending and axial deflections are arranged to occur in the spring section 1$b$ (within its own confines) between the most-distal tip portion 1$a$ and the proximal tip portion 1$c$. The mirror reflecting surface is typically metallic and the mirror can be nonfocusing or focusing. The ablator tip 1 may be an RF ablator tip wherein the most-distal portion 1$a$ is an RF electrode as the ablation member (e.g., made of metal such as a platinum alloy), or the ablator tip 1 may include one or more RF electrodes such as ring electrodes to provide RF ablation.

In FIG. 1$a$, the ablator tip 1 is depicted pressed into an endocardium 4 from a blood chamber 5 by the action of a contact force which generally will have a tangential component along the x-axis and a normal component along the y-axis. A directional (emitting in the −x direction here) ultrasonic transducer 3 is shown mounted in the rigid proximal tip portion 1$c$. The transducer 3 produces acoustic signals such as acoustic beams or acoustic pings leftwards along a −x beam path off the mirror 2 into the tissue 4 to a tissue focus 7 and receives reflection echoes back from the tissue 4, both defined by beam boundaries 6$a$ and 6$b$. Note that the surface of the mirror 2 will slightly move/reorient relative to the transducer 3 upon tip loading because they are separated by the slightly flexible spring portion 1$b$. FIG. 1A shows a slight bending of the tip, to an angle θ, perhaps a few degrees or so. A lesion 4$a$ is shown being formed in the tissue 4 as would be expected for an irrigated tip 1 with coolant saline 12 emanating from a beam port 11. Thus, the spring deflections are only large enough to detect tip forces (axial x force, radial y force, and/or their vector sum and its angle to the tip long axis). The deflections are not large enough to change the lesion feedback acoustic behavior is significantly different from that of a completely rigid acoustic transducer-mirror tip, i.e., the slight deflections do not shift the lesion feedback beam significantly.

According to one configuration of the catheter device, a totally rigid side-fire mirror tip (no force capability) is capable of lesion feedback and has shown good tissue spectra upon lesioning. The device has a hole or port 11 out of which the beam 6a/6b and the saline 12 emanate. That arrangement means that the RF lesion is formed primarily by the surrounding circumferential lip region of the most-distal tip portion 1a defining the hole or port 11 and somewhat by the saline 12 emanating therefrom. That also means that the tissue being lesioned has a free underwater surface as opposed to a physically trapped cooled-ablator pressing upon it. That might undesirably allow for easier boiling. We have shown that an open port 11 can be made to work with sufficient irrigation flow; however, this disclosure also covers a port being a conductive impermeable or permeable membrane or window or mesh which can itself deliver some RF energy. A nonconductive membrane is also within the scope of this disclosure.

The acoustic reflection/redirection member (mirror, window, or membrane) 2 and its movement relative to the transducer 3 form the force/deflection sensing mechanism. One preferred approach is the use of an angled (e.g., about 45 degrees as shown) acoustic mirror 2 stood off by a tip-internal saline cavity (between the mirror 2 and the transducer 3). We include in the scope of this disclosure the conditioning of the mirror (or membrane) surface (or bulk) such as by slight roughening, porosity or shaping so as to improve the mirror's acoustic visibility and response to orientation/position changes but not so much that we lose sensitivity otherwise useable for tissue reflections. The angled mirror, which is arranged to be nearly totally reflective (e.g., about 90-98%) but not 100% reflective, can thereby return both a virtually unaltered tissue reflection as well as a weaker tissue-nonobscuring reflection from the mirror itself.

Figure 4:
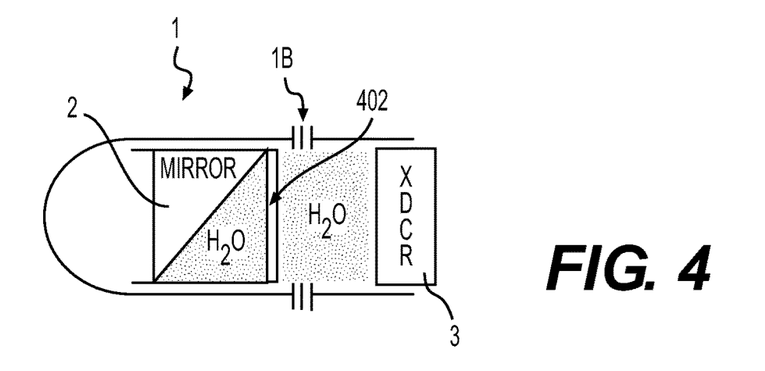
FIG. 4 shows an example of using two separate components for tissue images and deflections respectively.
Figure 5:
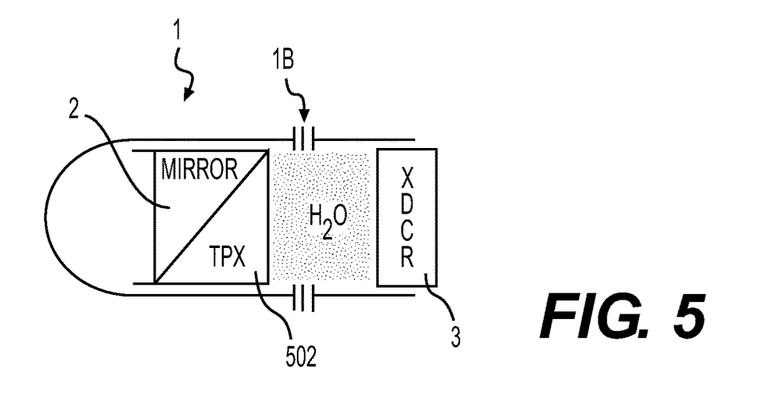
FIG. 5 shows another example of using two separate components for tissue images and deflections respectively.

Alternatively one may provide the above mirror for tissue feedback and along the same beampath and also inside the tip also provide a low loss window, membrane, or prism of TPX polymer whose job it is to provide a normally orthogonal weak reflector to detect deflections. FIG. 4 shows an example of using two separate components for tissue images and deflections respectively. The ablator tip 1 uses the acoustic mirror 2 to redirect the acoustic signal from the transducer 3 for tissue images and uses another member 402 to detect deflections. The member 402 may be a membrane of TPX (polymethylpentene) polymer which is more than 90% transparent but not 100% transparent. The mirror 2 and the membrane 402 form an acoustic reflection/redirection member. FIG. 5 shows another example of using two separate components for tissue images and deflections respectively. The ablator tip 1 uses the acoustic mirror 2 to redirect the acoustic signal from the transducer 3 for tissue images and uses another member 502 to detect deflections. The member 502 may be a solid prism of TPX polymer which is more than 90% transparent but not 100% transparent. The mirror 2 and the prism 502 form an acoustic reflection/redirection member.

The semi-rigid tip portion 1b may be made in a manner somewhat similar to a lasered Coolflex™ tip (i.e., using Nitinol™ tubing and a laser beam cutter to form through-thickness cuts or partial-thickness cuts/grooves). In the example shown in FIG. 1A, multiple rows of circumferential cuts are staggered to form the semi-rigid tip portion 1b. The major difference is that the laser cuts in this case are arranged to offer only very slight distortions (axial and/or angular) of the lasered member and are highly localized along the tip length dimension. The minimal distortion, semi-rigid spring member 1b can be provided in multiple ways and the following are a few examples. Some of these do not even involve laser cutting.

Approach 1—Use a laser machined metallic tube with significantly fewer laser cuts than a Coolflex™ flexible tip. The structure becomes much stiffer and acts as a stiff-spring to provide axial deflection of less than about 1 mm, preferably less than about 0.5 mm but more than about 0.125 mm and angular deflection of less than about ±10 degrees, preferably less than about ±5 degrees. Alternatively, the metallic tube may be machined in any manner such as by wet etching or EDM (electric discharge machining).

Approach 2—Use cuts which do not overlap as much, thereby reducing cumulative distortion. The structure becomes much stiffer.

Approach 3—Use a thicker tubing than a Coolflex™ flexible tip. The structure is linearly stiffer with increasing thickness approximately.

Approach 4—Rather than laser cutting of tubing, use instead a convoluted or bellows-like tubular entity, whether metallic, ceramic, glass or polymeric (e.g., uncut bellows-like electrodeposited shell tips, wave washers).

Approach 5—Make a flexible tip out of elastic braid to form a braided or woven tube, a mesh structure, a honeycombed sheet, or a polymeric tube. A tube is a body having an interior cavity, two open opposed ends, a length, and a cross-sectional shape mountable in or on the tip, the cross-sectional shape not necessarily round.

In FIG. 1A, the mirror 2 is mounted in the most distal rigid tip portion 1a and the transducer 3 is mounted in the proximal rigid tip portion 1c. In another embodiment, the transducer 3 is mounted in the most distal rigid tip portion 1a and the acoustic reflection/redirection member (mirror, window, or membrane) is mounted at the proximal rigid tip portion 1c or at the more proximal end of at least some of the connected semi-rigid deflectable portion 1b, the acoustic beam or ping traveling through the interior space of at least some of the deflectable semi-rigid portion 1b. The space for the acoustic path of the beam between the acoustic reflection/redirection member 2 and the transducer 3 includes or is filled with a flowable or deflectable low-acoustic-attenuation material such as saline or a low loss polymer such as a urethane or TPX or a combination thereof.

Typically, an operating transducer frequency of the transducer 3 is in the range of about 2 to 50 MHz with a preferred frequency in the range of about 10 to 30 MHz as a tradeoff between axial resolution and manufacturability. RF ablation and ultrasonic pinging are arranged to occur substantially separately in time to avoid their interfering with each other. Any one or more of RF ablation or ultrasonic pinging may be synchronized or gated using a biological signal such as an ECG or EGM signal in addition to or instead of being synched to each other directly.

Figure 1B:
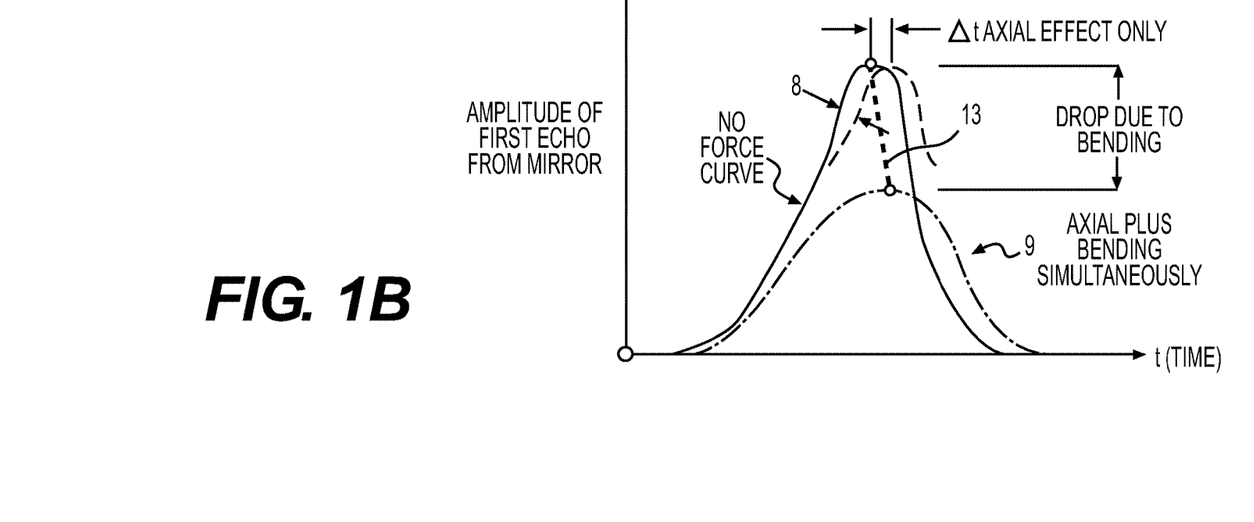
FIG. 1B shows plots of axial and radial (angular) deflection versus detected acoustic reflection amplitude from the mirror.

An example of the acoustics amplitude and/or time-phase variation versus tip forces is shown in FIG. 1B. The axial force component upon the tip along the ±x axis is the easiest to describe. Essentially any acoustic spectrum feature which occurs at a point in time will be shifted by Δt (see shifting of graph 8 in FIG. 1B) by the application of the axial force component. This is simply because the transducer 3 is either slightly closer to or slightly further from the mirror 2 (whose own reflection can be seen independent of the tissue reflections) for compression and tension tip loads, respectively. This phenomenon will take place even if there is also a few degree angular A for bending. The bending reflection variation behavior is approximately shown as a plot 9 at a particular axial deflection. Essentially over the narrow allowable 0-70 gram 0-5 degree or so bending range, the behavior will be slightly curvilinear as depicted. Although in the actual case, both axial and bending forces are simultaneously applied, what is occurring is that because of the heartbeat and/or breathing cycle, we will, over the time of seconds, be essentially plotting a back and forth orbital path such as the repeating path 13 shown in FIG. 1B. We anticipate that having that path information will allow us to deconvolute the axial and radial deflection components whatever combination they take. The transducer 3 can detect the deflection (axial and angular) via at least one of amplitude change or phase change of reflection of an acoustic signal reflected back from the acoustic reflection/redirection member 2. In a preferred embodiment, the mirror angulation itself causes minimal time-delay change (but a large amplitude change) and if desired, by knowing the amplitude change (and bending degree), one can actually subtract out the minimal time-delay change due to bending such that all remaining time delay change is due to axial deflection. The inventors have demonstrated this ability albeit the correction is small.

In US2012/0265069 (which is incorporated herein by reference in its entirety), we taught an acoustically transparent RF tip made substantially entirely of carbon (e.g., at least about 90% carbon by volume) having an acoustic impedance between that of the transducer and that of the tissue. As applied in this case, the rigid most-distal portion 1a may be carbon based such that there is no need for an open port 11, resulting in the delivery of uniform RF. One would still have irrigated saline very close by or upon the heated tissue surface. Furthermore, the mirror 2, with a carbon tip portion 1a, may be a thinfilm metal-on-carbon laminate.

The catheter provides ablation capability in addition to at least one of (a) data regarding a formed or forming lesion, (b) data regarding an interface or tissue thickness, (c) data regarding a degree of transmurality of a lesion in a tissue layer, and (d) data regarding potential or actual pop activity. Either of lesion-feedback or pop potential is detected acoustically by an acoustic beam which enters tissue through the acoustic reflection/redirection member 2 (mirror, window or membrane) or an open hole or port 11 in the tip 1. Furthermore, (i) any one or more of force, a lesion progress parameter or a pop parameter are reported to the user in any form; (ii) any one or more of force, a lesion progress parameter or a pop parameter are internally utilized by the system in any form; and (iii) any one or more of force, a lesion progress parameter or a pop parameter are recorded or remotely communicated in any form. By allowing the acoustic beam or ping to enter tissue, the system also or instead reports or utilizes any one or more of: (i) lesioning behavior or state, (ii) prepop behavior or state, and (iii) proximity or orientation to tissue. Any one or more of the force, pop or lesion-feedback capabilities may be activated and/or deactivated via software uploads, network communications, or customer input, whether by the system user, by a connected system or network or by a remote support person. Any one or more of force, a lesion progress parameter, or a pop parameter may be utilized as feedback to the system or user for a control, safety, or logging reason.

If a customer has possession of a transducer-bearing catheter, we can provide or activate software, even remotely, which can perform any one or more of: (a) reporting force, (b) providing anti-pop monitoring, and (c) reporting lesion depth. Since upon pinging we get all the information pertaining to the tissue and the moving mirror, we are not adding anything to procedure time. The algorithm to do the distortion measurement (force measurement) is actually much simpler than the lesion-depth algorithm or the anti-pop algorithm. We can provide software upgrade on-demand at the moment the practitioner decides he/she wants that modality. It would be turned on and charged to the customer's account at the same time.

We stated that macroscopically conforming lasered bending tips teach away from the present invention. That is because if one simply puts the inventive transducer and mirror on the opposite (far) end of such a flexible laser tip, the tissue-conformance bending is so large (tens of degrees bending sometimes) that it would be very difficult to retain a reasonable tissue-echo spectrum from the tissue or, for that matter, any echo off the mirror back to the transducer over such a huge range. Although one could put the transducer and mirror closer together to overcome this issue, when one does that, one is removing some of the useful standoff distance which allows easy identification of the mirror echo beyond the transducer ringing noise. However the invention is not fundamentally incompatible with highly conforming macroscopically bending tips. By placing the mirror closer to the transducer, one could tolerate more tip bending as long as the transducer employed has a short enough ringdown.

Figure 6:
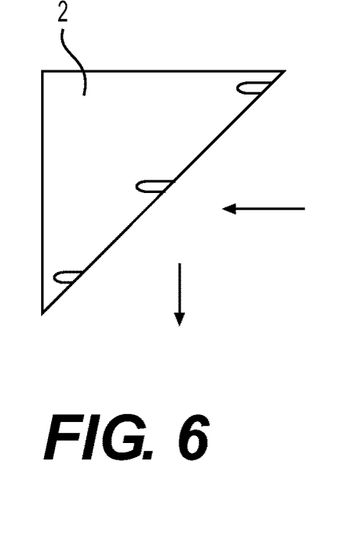
FIG. 6 shows an example of a mirror having a microstructured surface in the form of a three holes at the mirror periphery distributed about 120 degrees apart from each other.
Figure 7:
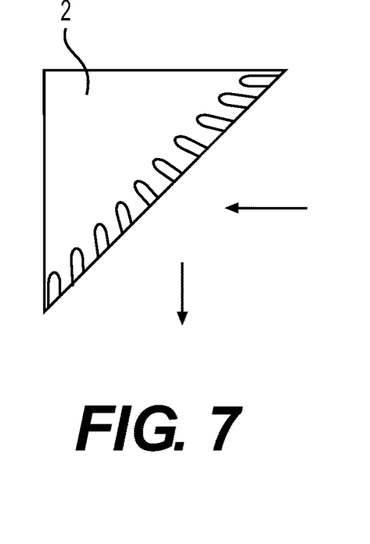
FIG. 7 shows an example of a mirror having a microstructured surface in the form of an array of holes along diagonal(s).

We also include in the scope of this invention the mirror 2 (or window or membrane) having a microstructured surface such as that made by laser machining or etching. The idea is to place features on/in the mirror surface either locally or across the mirror face (a) which do not substantially interfere with tissue echoes such as by consuming only a very small percentage of the area of the mirror (e.g., a few percent at the midregion for example) and (b) which enhance the changes in acoustic reflection behavior (amplitude and/or phase) with mirror tilting and/or axial motion. For example, one could laser drill an array of holes at ever increasing angles from 90 degrees into the mirror surface. The ability to acoustically "see" the bottoms of the various holes depends on whether that particular angled hole is "pointing" at the transducer at that particular state of bending load. Such a hole array could be placed in the central mirror region and/or concentrated upon a few radial lines running from mirror center to edge. FIG. 6 shows an example of a mirror 2 having a microstructured surface in the form of a three holes at the mirror periphery distributed about 120 degrees apart from each other. FIG. 7 shows an example of a mirror 2 having a microstructured surface in the form of an array of holes along diagonal(s). The holes come/go from acoustic view versus tilt angle. The hole bottoms provide strong orthogonal reflectors at zero degrees. Varying hole depth could allow identification of any specific hole.

The mirror 2 (or window or membrane) may also be focusing or refracting of acoustics wherein the acoustic reflections from the mirror vary with angle as the reflection/focus/refraction behavior versus angle systematically changes.

One feature the invention is a combined acoustic and optical solution wherein the acoustics do the lesion feedback, the antipop monitoring, and only the axial part of force detection. The mirror is optically coated with an optical interference film system such that its optical reflectivity (or reflected color) changes with mirror tilt angle. In this case, a small optical fiber/optical lens/light source would illuminate the mirror likely in the middle from a standoff distance larger than the maximum tip compression. The reflected light would be analyzed for color and/or amplitude. Thus we get bending force optically from the mirror and we get axial force acoustically from the mirror.

We again expect and know that when an intracardiac or other therapeutic or diagnostic catheter is in the body that the heartbeat motion, the blood flow and the breathing of the patient all cause periodic variations in catheter tip contact angle and force. We include here in our inventive scope, most particularly for those applications involving lesion or pop feedback, the recording or use of known instrumented breathing rates and heartbeat rates in order to account for their effects upon echograms. For example, echograms could be time-sampled based on the heartbeat deduced from the cyclic force data thereby obtaining echograms at known heartbeat phase angles. As an alternative one can record enough echograms often enough so that such periodicities can be discovered purely from the echogram data and the appropriate compensations made therefore.

Figure 2:
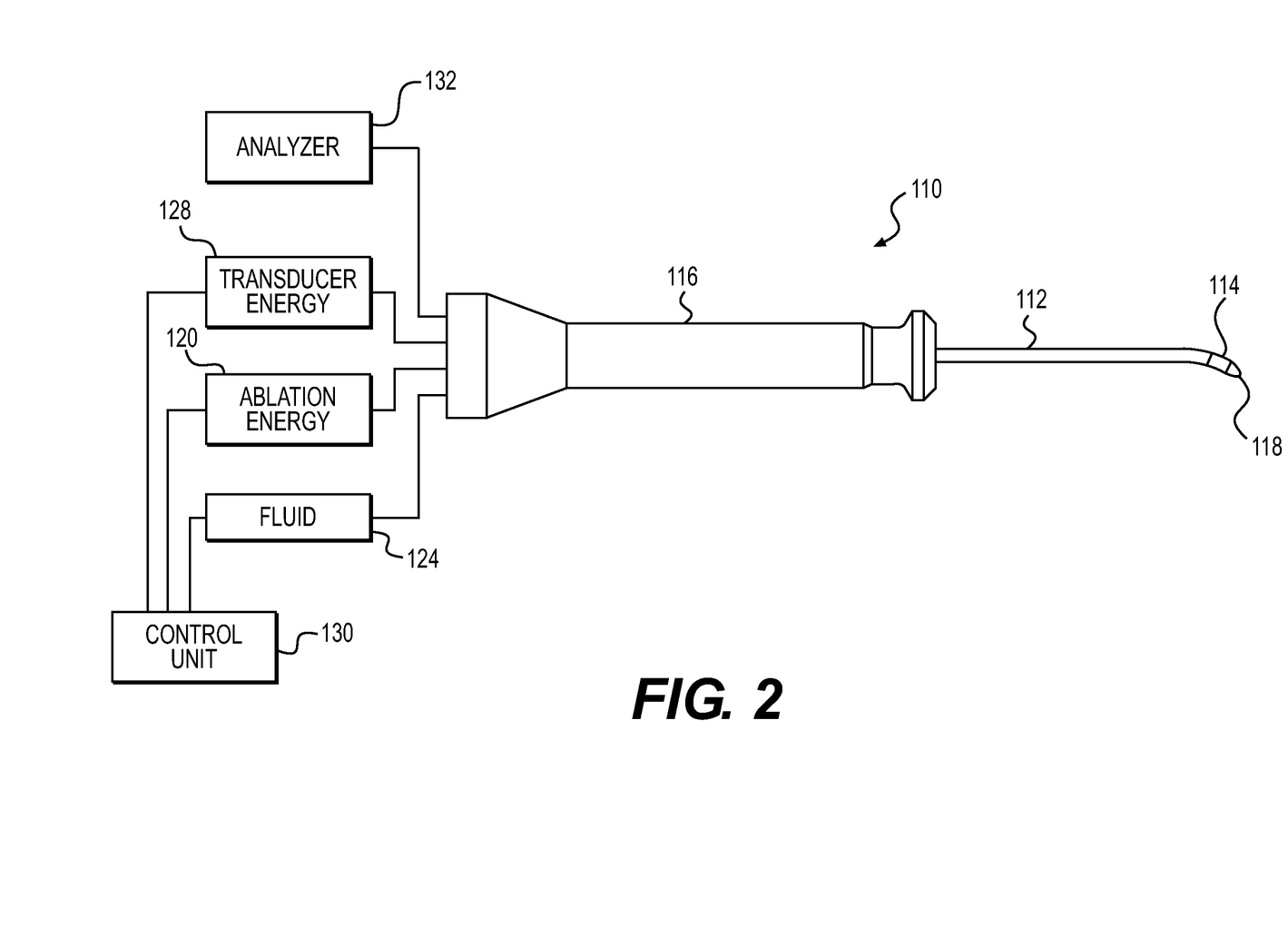
FIG. 2 is a schematic diagram of an ablation apparatus incorporating the ablation catheter tip of FIG. 1A.

FIG. 2 is a schematic diagram of an ablation apparatus incorporating the ablation catheter tip of this disclosure. An ablation catheter 110 includes a control handle 116, and an elongated catheter body 112 having a distal region 114 adjacent a distal end 118. The distal region 114 includes any of the ablation tips shown and described herein (e.g., ablator tip 1 in FIG. 1A or ablating tip 302 in FIG. 3). The catheter 110 is connected with an ablation energy source 120 such as an RF generator, and with an irrigation fluid source 124 to provide an irrigation and tip-cooling fluid. A transducer pinger 128, which might have more than one channel, transmits and receives pinging energy such as that delivered to or received from acoustic transducer(s) (e.g., 3 in FIG. 1A or 305a and 305b in FIG. 3). A control unit or controller 130 is provided for controlling the ablation and the acoustic pinging during ablation. For instance, the control unit 130 is configured to carry out the duty cycles for ablation and pinging. An acoustic pinger echo analyzer 132 is provided to analyze the data collected (e.g., by a software or firmware algorithm) from the acoustic transducer(s) to provide one or more of lesion feedback, tissue thickness or proximity measurement, tip contact force monitoring, and pre-pop detection. The information is preferably presented to the operator (e.g., using a graphical user interface) to provide real time assessment of the ablation. The information may additionally or alternatively be utilized by the system itself without operator intervention. Based on a detected deflection and a related force-deflection relationship of the deflectable spring portion 1b, the control unit 130 can determine the force between the distal tip 1 and the biological member such as the endocardium 4.

Figure 3:
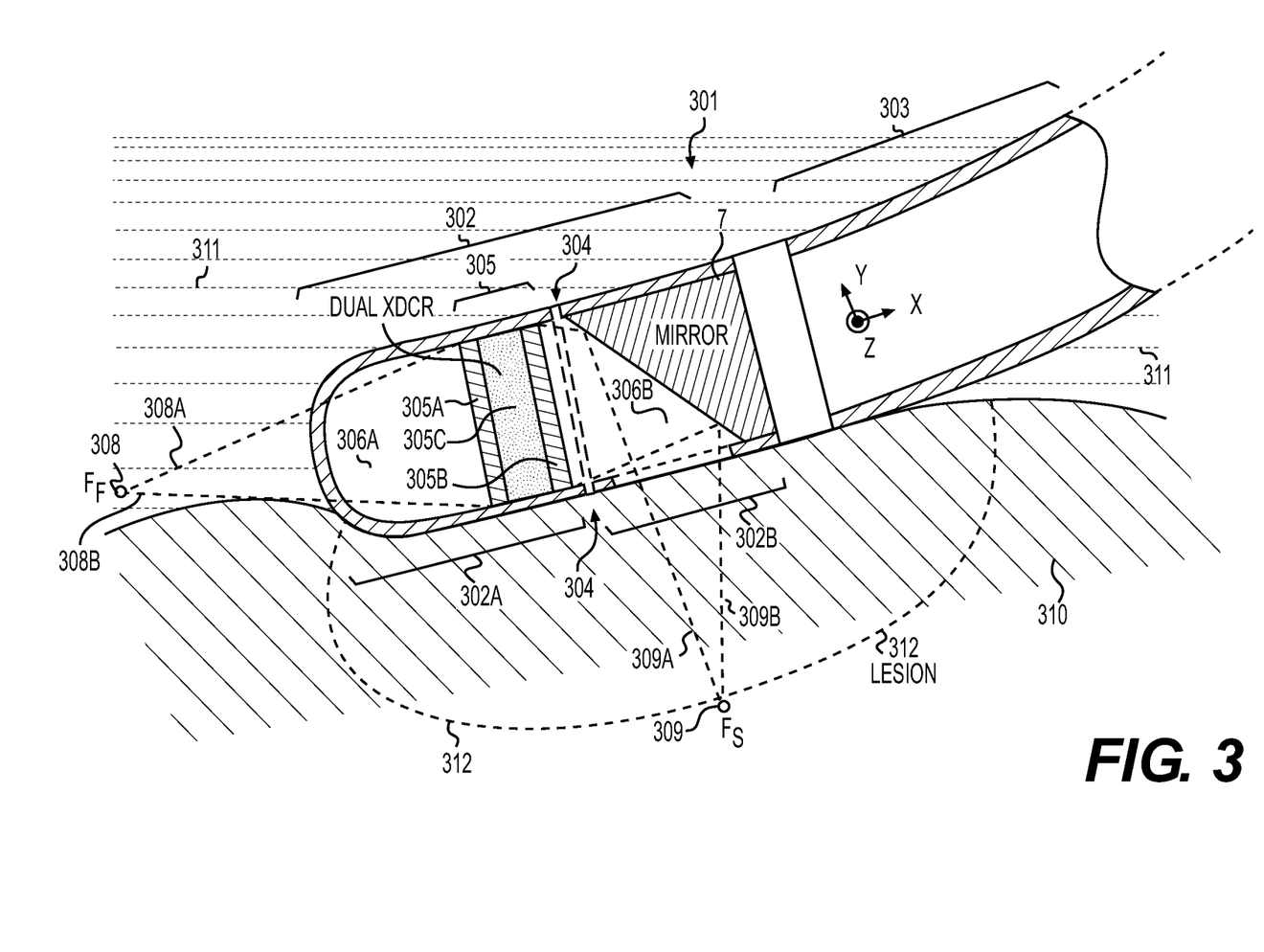
FIG. 3 shows another catheter tip region illustrating a dual transducer with forward and side looking ultrasonic lesion feedback and optional force detection.

Ultrasonic Feedback with Forward and Side Looking Acoustic Transducers in Semirigid Catheter Tip FIG. 3 shows another catheter tip region illustrating a dual transducer with forward and side looking ultrasonic lesion feedback and optional force detection. FIG. 3 shows an RF ablation catheter 301 having an ablating tip 302 distally mounted on a flexible catheter body 303 having a lumen. The catheter 301 is shown immersed in blood 311 such as within a heart chamber or some other biological member. The catheter ablation tip portion 302 is depicted resting against a myocardial or ventricular wall 310 which is to receive a lesion 312. It will be noted that the distal tip portion 302 contains a dual ultrasonic transducer 305 capable of either or both of pinging forwardly along the −x direction or downwardly (sideways via mirror 307 redirection) in the −y direction. The transducer 305 has a shared common attenuative backer material portion 305c on which are mounted opposed piezotransducers 305a (forward looking) and 305b (side looking via redirecting acoustic mirror 307). Because the transducer piezoelements 305a/305b both share the same attenuative backer 305c, we save space inside the tip 302. The forward firing transducer 305a forms a beam defined by beam outline 308a/308b which comes to a forward focus at point 308 also labeled as $F_f$. That forward beam passes through a window or hole in the tip body in order to pass to focus 308. The side-firing (via mirror 307) transducer 305b forms a beam which is redirected sideways (−y direction) in the form of outline 309a/309b and coming to a focus at point 309 also labeled as point $F_s$. The acoustic mirror 307, such as a stainless mirror, is depicted to have a 45 degree angle relative to the x-axis such that it redirects the sidefire beam 309a/309b approximately at a right angle out of the tip 302 into the target tissue 310.

It will be noted in FIG. 3 that the forward-firing beam 308a/308b travels through saline 306a or other acoustically transparent material (such as urethane, silicone, or TPX) before emanating forwardly generally along the longitudinal axis to focus point 308. Likewise, sidefire beam 309a/309b travels through saline or other acoustically transparent material 306b before emanating sideways in a beam emanation direction to focus point 309 ($F_s$). In a preferred embodiment, materials 306a and 306b are saline which is passed through the tip 302 also for cooling purposes (such as for tissue surface cooling/irrigation and/or tip cooling). Included within the inventive scope is having portions of the saline filled region instead or partly filled with the aforementioned transparent, nonfluid, flexible or rigid materials such as urethane, silicone, or TPX.

The distal ablating tip 302 includes a first ultrasonic transducer 305a oriented to give a tip-forward view of target tissue 310 (in the forward direction along the longitudinal axis, when the tip is end-on to tissue) and a second ultrasonic transducer 305b oriented to give a tip-sideways view of target tissue 310 (acoustic signal being redirected in a transverse direction nonparallel to the longitudinal axis and typically substantially perpendicular to the longitudinal axis) as shown in FIG. 3. At least one of the transducers (305b) directs its acoustic beam upon the acoustic redirection mirror 307 which redirects the acoustic beam to achieve its sideways view of target tissue 310. The transducer 305b and the acoustic mirror 307 are situated on opposite sides of a tip spring member 304 of known stiffness which distorts in response to a tip load causing an angle and/or distance between the transducer 305b and the mirror 307 to vary with the tip force, the distortions (bending and axial) each being acoustically detectable and accompanied by a corresponding tip force component. In FIG. 3, the dual transducers 305 are mounted to a rigid most-distal tip portion 302a while the mirror 307 is mounted to a rigid proximal tip portion 302b. The two transducers 305a, 305b are mounted in an opposed fashion such that they share a common attenuative backer 305c rather than separate backers which would take more space. Each of the transducers is separately operable via its own electrical interconnections (not shown).

As seen in FIG. 3, the distal tip 302 has lasered slits or slots cut into it at a localized axial location to form an intermediate semi-rigid spring portion 304. These slots act as a stiff spring such that the more distal tip portion 302a can slightly deflect angularly with respect to the more proximal tip portion 302b such as around one or both of the y-axis and/or z-axis. The semi-rigid portion 304 may also/instead allow some stiff axial deformation axially along the x-axis. By stiff we mean that typical tip loads in the range of about 10-100 grams will bend the most-distal tip portion 302*a* relative to the proximal tip portion 302*b* just a few degrees at most (less than about 10 degrees, preferably less than about 5 degrees). In this manner, even when bent by a tip-load, the side-fire beam 309*a*/309*b* can still echogenically view the tissue. The same can be said for any axial deflection of the stiff spring 304 in that it may be limited to a fraction of a millimeter or even less (less than 1 mm, preferably less than about 0.5 mm), as long as it is acoustically detectable as a moved reflection in the time domain. In specific embodiments, the axial deflection is less than about 1 mm under an axial force of less than about 100 grams. The bending deflection is less than about 10 degrees under a bending moment of about 200 gram-millimeters (e.g., 100 grams applied at 2 mm moment arm distance from the tip spring member 304, 2 mm being the likely length of the most-distal tip portion 302*a*).

As taught in the earlier disclosure, one monitors the echo reflections from the surface of the mirror 307 in order to deduce and back-compute deflections of the stiff spring 304. Two or more deflections may be evaluated in order to provide a vector sum and subcomponents of the net vector sum tip force. The mirror echoes are preferably significantly weaker (e.g., 5-20 times) than the tissue echoes and arrive at an earlier time so that they can be differentiated from each other.

In the typical case the practitioner or doctor would, at a given moment, be using either the forward firing or the side firing transducer depending on which has the best view of the tissue portion to be lesioned. In FIG. 3, the lesion 312 is best viewed by the side-firing transducer 305*b* and its redirected beam 309*a*/309*b*. The lesion 312 is regarded as a sideways lesion as opposed to an end-on lesion. The system used to control the catheter could automatically acoustically recognize that there is tissue in front of (in the beamline of) a given transducer 305*a* or 305*b* and switch over to that transducer.

The described embodiments, as those familiar with acoustics will recognize, typically have the mirror or mirror and window/membrane in the near-field of the transducer beam pattern. Inventors explicitly include in their scope embodiments operating in the beams far-field as well. It will be appreciated that near-field operation may allow for a shorter tip which is preferable.

Herein we have taken the liberty of giving force as grams which is often done for tip forces; however, the astute and technically correct reader will understand that such practitioners mean grams-force and not grams- mass. That is, the force or weight of a 1 gram mass is one gram-force in earth gravity.

While specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. An method for monitoring a medical procedure, comprising:
    providing a catheter comprising:
        an elongated catheter body extending longitudinally between a proximal end and a distal end along a longitudinal axis;
        a distal member disposed adjacent the distal end and including a most-distal portion, a proximal portion, and a deflectable portion between the most-distal portion and the proximal portion to permit deflection between the most-distal portion and the proximal portion of the distal member, the deflectable portion being more deflectable than at least one of the most-distal portion or the proximal portion;
        an acoustic transducer disposed in the distal member and configured to emit acoustic energy toward a biological member and receive reflection echoes therefrom; and
        an acoustic redirection member disposed in the distal member to at least partially redirect the acoustic energy emitted from the acoustic transducer toward a tissue target,
        wherein one of the acoustic transducer and the acoustic redirection member is mounted to the proximal portion of the distal member and the other of the acoustic transducer and the acoustic redirection member is mounted to the most-distal portion of the distal member;
    directing an acoustic signal from the acoustic transducer to the biological member;
    receiving reflection echoes of the acoustic signal from the biological member at the acoustic transducer; and
    detecting a deflection between the most-distal portion of the distal member and the proximal portion of the distal member based on the received reflection echoes of the acoustic signal.

2. The method according to claim 1, wherein the detecting comprises detecting the deflection via at least one of an amplitude change, a phase change, or a time-delay change of a reflection of the acoustic signal reflected back from the acoustic redirection member to the acoustic transducer.

3. The method according to claim 1:
    wherein the catheter further comprises an acoustic reflection member mounted to a common portion of the distal member with the acoustic redirection member to partially reflect the acoustic signal back to the acoustic transducer, and
    wherein the detecting comprises detecting the deflection at least one of an amplitude change, a phase change, or a time-delay change of a reflection of the acoustic signal back from the acoustic reflection member.

4. The method according to claim 1, further comprising determining a force acting on the distal member based on the detected deflection and a known relationship between force acting on the distal member and deflection of the deflectable portion of the distal member.

5. The method according to claim 1, wherein the acoustic signal comprises one of an acoustic beam or an acoustic ping.

6. The method according to claim 1, wherein the directing comprises at least one of:
    directing a first acoustic signal from the acoustic transducer in a direction generally parallel to the longitudinal axis of the elongated catheter body to the acoustic redirection member, which redirects the first acoustic signal in a transverse direction non-parallel to the longitudinal axis of the elongated catheter body; or directing a second acoustic signal from the acoustic transducer in a direction generally parallel to the longitudinal axis of the elongated catheter body.

7. The method according to claim 1, wherein directing the acoustic signal to the biological member and receiving the reflection echoes of the acoustic signal from the biological member comprises analyzing at least one of a tissue thickness measurement in the biological member and a tissue proximity to the biological member.

8. The method according to claim 1, wherein the deflectable portion of the distal member permits at least one of axial deflection along the longitudinal axis of the elongated catheter body or bending deflection between the most-distal portion of the distal member and the proximal portion of the distal member.

9. The method according to claim 8, wherein the axial deflection is less than 1 mm under an axial force of less than 100 grams-force.

10. The method according to claim 8, wherein the bending deflection is less than 10 degrees under a bending moment of about 200 grams-force-millimeters.

11. A system for monitoring a medical procedure, comprising:
a catheter comprising:
an elongated catheter body extending longitudinally between a proximal end and a distal end along a longitudinal axis;
a distal member disposed adjacent the distal end and including a most-distal portion, a proximal portion, and a deflectable portion between the most-distal portion and the proximal portion to permit deflection between the most-distal portion and the proximal portion of the distal member, the deflectable portion being more deflectable than at least one of the most-distal portion or the proximal portion;
an acoustic transducer disposed in the distal member and configured to emit acoustic energy toward a biological member and receive reflection echoes therefrom; and
an acoustic redirection member disposed in the distal member to at least partially redirect the acoustic energy emitted from the acoustic transducer toward a tissue target,
wherein one of the acoustic transducer and the acoustic redirection member is mounted to the proximal portion of the distal member and the other of the acoustic transducer and the acoustic redirection member is mounted to the most-distal portion of the distal member;
a transducer pinger configured to:
direct an acoustic signal from the acoustic transducer to the biological member; and
receive reflection echoes of the acoustic signal from the biological member at the acoustic transducer; and
an analyzer configured to detect a deflection between the most-distal portion of the distal member and the proximal portion of the distal member based on the received reflection echoes of the acoustic signal.

12. The system according to claim 11, wherein the analyzer is configured to detect the deflection via at least one of an amplitude change, a phase change, or a time-delay change of a reflection of the acoustic signal reflected back from the acoustic redirection member to the acoustic transducer.

13. The system according to claim 11:
wherein the catheter further comprises an acoustic reflection member mounted to a common portion of the distal member with the acoustic redirection member to partially reflect the acoustic signal back to the acoustic transducer, and
wherein the analyzer is configured to detect the deflection via at least one of an amplitude change, a phase change, or a time-delay change of a reflection of the acoustic signal back from the acoustic reflection member.

14. The system according to claim 11, wherein the analyzer is further configured to determine a force acting on the distal member based on the detected deflection and a known relationship between force acting on the distal member and deflection of the deflectable portion of the distal member.

15. The system according to claim 11, wherein the acoustic signal comprises one of an acoustic beam or an acoustic ping.

16. The system according to claim 11, wherein the transducer pinger is configured to at least one of:
direct a first acoustic signal from the acoustic transducer in a direction generally parallel to the longitudinal axis of the elongated catheter body to the acoustic redirection member, which redirects the first acoustic signal in a transverse direction non-parallel to the longitudinal axis of the elongated catheter body; and
direct a second acoustic signal from the acoustic transducer in a direction generally parallel to the longitudinal axis of the elongated catheter body.

17. The system according to claim 11, wherein the transducer pinger is configured to analyze at least one of a tissue thickness measurement in the biological member and a tissue proximity to the biological member.

18. The system according to claim 11, wherein the deflectable portion of the distal member permits at least one of axial deflection along the longitudinal axis of the elongated catheter body or bending deflection between the most-distal portion of the distal member and the proximal portion of the distal member.

19. The system according to claim 18, wherein the axial deflection is less than 1 mm under an axial force of less than 100 grams-force.

20. The system according to claim 18, wherein the bending deflection is less than 10 degrees under a bending moment of about 200 grams-force-millimeters.

* * * * *